United States Patent [19]
Carter et al.

[11] Patent Number: 5,811,593
[45] Date of Patent: Sep. 22, 1998

[54] MONOACETALS OF HYDROQUINONE

[75] Inventors: John David Carter, Cincinnati, Ohio; Jack Lee Parsons, East Aurora; David Fred Starks, Williamsville, both of N.Y.

[73] Assignee: The Procter & Gamble Company, Cincinnati, Ohio

[21] Appl. No.: 747,479

[22] Filed: Nov. 12, 1996

Related U.S. Application Data

[62] Division of Ser. No. 357,849, Dec. 16, 1994, Pat. No. 5,585,525.

[51] Int. Cl.$^6$ .................................................. C07C 43/307
[52] U.S. Cl. ........................... 568/592; 549/416; 549/475
[58] Field of Search .............................. 568/592; 549/416

[56] References Cited

U.S. PATENT DOCUMENTS 5,585,525  12/1996  Carter et al. ............................ 568/592

FOREIGN PATENT DOCUMENTS

0383319 A2   8/1990   European Pat. Off. ....... C07D 471/04
1423073      1/1976   United Kingdom .......... C07C 149/42

OTHER PUBLICATIONS

Lam et al. "The Syntheses of Phenolic Antioxidants, 1,3,5–Tris(4–Hydroxyphenoxymethyl) Mesitylene and Related Compounds", *Organic Prepartions and Procedures Int.*, vol. 14(4), pp. 241–247 (1982).

Lam et al. The Syntheses of Phenolic Antioxidants. 3,5–Bis(3,5–Di–Tert–Butyl–4–Hydroxybenzyl)–2,3,6–Trimethylbenzyl Derivatives *Organic Preparations and Procedures Int.* vol. 14(5), pp. 309–317 (1982).

Bieg and Szeja, "Removal of O–Benzyl Protective Groups by Catalytic Transfer Hydrogenation", *Communications,* Jan. 1985.

Bieg and Szeja, "Cleavage of 2–Phenyl–1,3–dioxolanes and Benzyl Ethers by Catalytic Transfer Hydrogenation", *Communications,* Apr. 1986.

Banik et al. "Microwave–Induced organic Reaction Enhancement Chemistry. 4 Convenient synthesis of Anantiopure α–Hydroxy–β–Lactams", *Tetrahedron Letters,* vol. 33, No. 25, pp. 3603–3606 (1992).

Krishnamurty et al., "Cleavage of Aryl Benzyl Ethers by Heteogeneous Catalytic transfer Hydrogenation", *Indian Journal of Chemistry,* Sec. B, vol. 25B, pp. 1253–1254, 1986.

Hanessian et al., "Facile Cleavage of Benzyl Ethers by Catalytic Transfer Hydrogenation", *Synthesis,* No. 5, pp. 396–397, May 1981.

*Primary Examiner*—Bernard Dentz
*Attorney, Agent, or Firm*—John M. Howell; Loretta J. Henderson; David L. Suter

[57] ABSTRACT

The present invention is for a process for preparing monoacetals of hydroquinone wherein said process provides for higher yields of greater purity. Said process utilizes a two step reaction wherein a protected hydroquinone is reacted with an enol ether to form a protected intermediate. Upon hydrogenolysis of said intermediate a final product, monoacetal hydroquinone, is formed having higher degree of purity and in greater yields that the yields attributed to reactions known in the art.

17 Claims, No Drawings

MONOACETALS OF HYDROQUINONE

This is a division of application Ser. No. 08/357,849, filed on Dec. 16, 1994, now U.S. Pat. No. 5,585,525.

FIELD OF THE INVENTION

The present invention is for a process for preparing monoacetals of hydroquinone wherein said process yields higher yields of greater purity than reactions previously used.

BACKGROUND OF THE INVENTION

The process for making monoacetals of hydroquinone is disclosed in co-pending patent application U. S. Ser. No. 08/206,573, filed Mar. 4, 1994 now abandoned; incorporated herein by reference. Said process involves reacting equimolar amounts of hydroquinone with enol ethers in the presence of an acid catalyst:

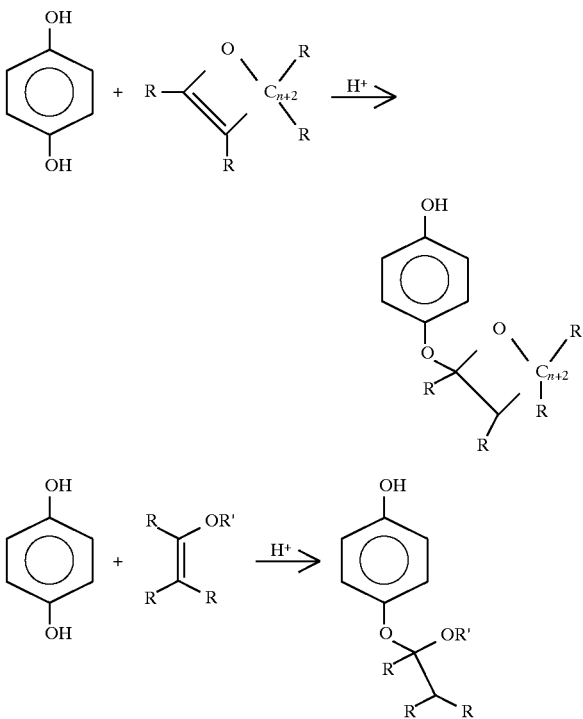

(i) each R is, independently, selected from the group consisting of hydrogen; $C_1$–$C_{10}$ alkyl; benzyl, aryl and substituted benzyl or aryl.

(ii) each R' is, independently, selected from the group consisting of $C_1$–$C_{10}$ alkyl; benzyl, aryl and substituted benzyl or aryl.

(iii) n is an integer from 0 to 3.

However, said reaction has several limitations. For equimolar concentrations of hydroquinone and enol ethers said reaction also results in formation of hydroquinone bis-acetals which are poor skin lightening compounds. Removal of the non-efficacious bis-acetal compounds, along with unreacted hydroquinone, necessitates expensive large scale chromatographic purification such that isolated yield of said monoacetal is poor, typically 30–40%. Attempts at improving overall yield and cost of process via conversion/recycling of bis-acetal to desired monoacetal is problematic due to similar reactivity of the two compounds, while changing the stoichiometry of the reaction to minimize bis-acetal formation increases the amount of hydroquinone which ultimately needs to be chromatographically removed.

SUMMARY OF THE INVENTION

The present invention is a process for preparing monoacetals of hydroquinone comprising the steps of:

a) reacting monoethers of hydroquinone with an enol ether in the presence of an acid catalyst to yield the protected monoacetal of hydroquinone as an intermediate; and b) reacting said intermediate with a hydrogen transfer source in the presence of a metal catalyst such that protecting group is selectively cleaved to give desired hydroquinone monoacetal.

These reactions produce purer hydroquinone monoacetals in high yield without the need for chromatographic purification.

DETAILED DESCRIPTION OF THE INVENTION

The present invention is a novel process for making hydroquinone monoacetals comprising a series of steps wherein monoethers of hydroquinone are used to improve the purity and the yield of the desired final product compared to the process previously disclosed. Reaction of said hydroquinone monoether with an enol ether yields an intermediate product that is protected from acid catalyzed coupling with a second equivalent of enol ether, irrespective of the stoichiometry of the monoether compound and enol ether. Utilization of protecting groups to eliminate production of undesirable by-products of synthesis reactions is well known in the art. In the present invention it is desirable to eliminate or at the very least minimize producing bis-acetal hydroquinone compounds, which if present at the time of the second process step of the present invention, yields undesirable final products. In the subsequent hydrogenolysis of said intermediate product, selective cleavage of ether protecting group provides the final desired product in higher yields with greater purity.

The hydroquinone protecting groups useful in the present invention are ethers susceptible to selective hydrogenolysis under mild conditions. Said ethers used as protective groups in the present invention are selected from the group consisting of arylmethyl, diarylmethyl, triarylmethyl, trimethylsilyl ethers and mixtures thereof, preferably arylmethyl ethers. The preferred arylmethyl ether protecting groups of the present invention are selected from the group consisting of benzyl, aliphatic benzyl ethers and mixtures thereof, preferably aliphatic benzyl ether, most preferably the monobenzyl ether. The monobenzyl ether of hydroquinone may be purchased as monobenzone or 4-(benzyloxy) phenol directly from commercial sources such as Aldrich Chemical Company and Hoechst Celanese Corporation. Monobenzone may also be produced by routine chemical reactions well known in the art; see Schiff and Pellizzari, *Justus Liebig's Annalen Der Chimie*, vol. 221, pp370 (1883); incorporated herein by reference.

The said hydroquinone monoether is reacted with cyclic or acyclic enol ethers to yield the protected intermediate, preferably the benzyl protected monoacetal of hydroquinone, as illustrated below:

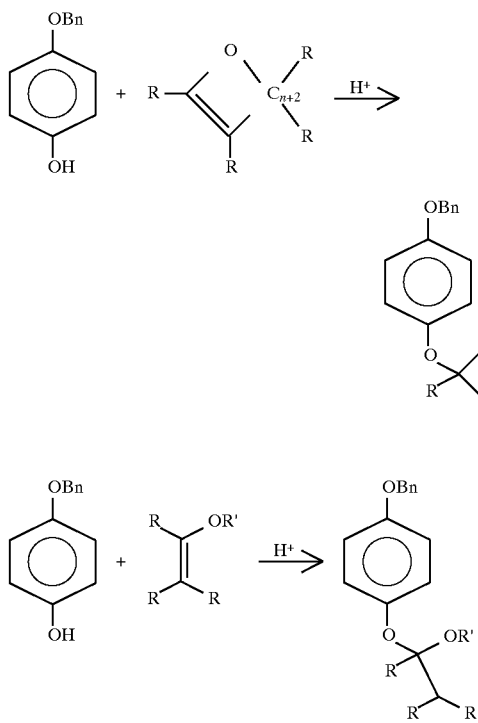

wherein:

(i) each R is, independently, selected from the group consisting of hydrogen; $C_1$–$C_{10}$ alkyl; benzyl, aryl and substituted benzyl or aryl.

(ii) each R' is, independently, selected from the group consisting of $C_1$–$C_{10}$ alkyl; benzyl, aryl and substituted benzyl or aryl.

(iii) n is an integer from 0 to 3; and po1 (iv) Bn is a benzyl group.

This intermediate product is then subjected to a subsequent hydrogenolysis reaction in order to cleave said benzyl protective group from the intermediate product above to provide the final desired product. Selective removal of hydroxyl protecting above to provide the final desired product. Selective removal of hydroxyl protecting groups including O-benzyl groups is known. Bieg and Szeja, *Removal of O-Benzyl Protective Groups by Catalytic Transfer Hydrogenation*, Synthesis, January 1985, discloses the cleavage of benzyl ethers of monosaccharides using ammonium formate as a hydrogen donor and 10% palladium on carbon catalyst. It is further disclosed therein that said method may be used for the selective removal of O-benzyl ethers in the presence of other types of O-protecting groups. Bieg and Szeja,*Cleavage of 2-Phenyl-1,3-dioxolanes and Benzyl Ethers by Catalytic Transfer Hydrogenation*, Synthesis, April 1986, discloses cleavage of 2-phenyl-1,3-dioxolane protective groups by catalytic transfer hydrogenation which circumvents the disadvantage of simultaneous cleavage of a 2-phenyl-1,3-dioxane group also present in the molecule. Hydrazine hydrate is used as the hydrogen source and 10% palladium on carbon as the catalyst. Said reaction may be utilized for preparation of a whole range of partially protected sugars.

In the present invention the hydrogenolysis step is as illustrated below:

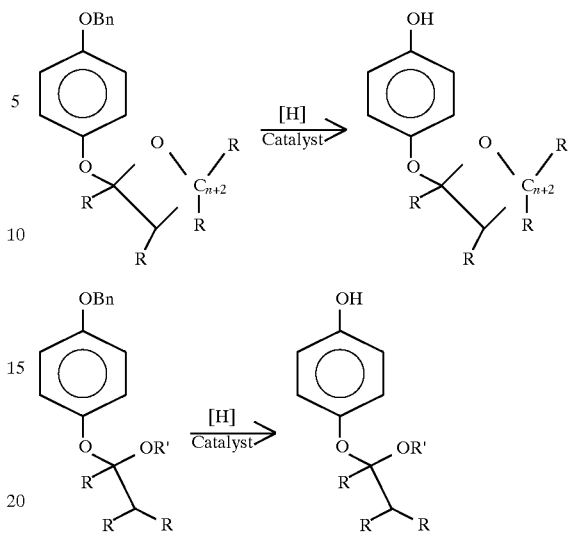

Cleavage of the benzyl group is accomplished in virtually quantitative yield with non-acidic hydrogen transfer sources such as hydrazine hydrate and ammonium formate in combination with a supported metal catalyst. The acetal portion of the intermediate molecule is unaffected by these conditions, eliminating the simultaneous formation of hydroquinone and/or regeneration of monobenzone. Hence there is no need for any chromatographic separation and the desired compounds can be isolated via simple purification techniques. Overall yield for the two step process is significantly higher than the previously disclosed one step process.

Reaction Method

A. STEP ONE

As disclosed above the first step of the process is to produce the protected intermediate. In the case of the benzyl protecting group, 4-(benzyloxy)phenol is combined with a cyclic or acyclic enol ether and a catalytic amount of acid under an inert atmosphere. In general, the stoichiometric ratio of enol ether and 4-(benzyloxy)phenol is from 1:1 to 2:1. A variety of acidic sources can be used, preferably those selected from the group consisting of hydrochloric acid, sulfuric acid, para-toluenesulfonic acid and mixtures thereof, wherein the catalytic dose does not exceed 0.02 equivalents based on the weight of 4-(benzyloxy)phenol. A typical dose is 0.005–0.015 equivalents of acid. Most preferred acidic source is hydrochloric acid.

Formation of the intermediate is conveniently carried out in a variety of polar organic solvents. Preferred polar solvents include those selected from the group consisting of methylene chloride, diethylether, tetrahydrofuran, dioxane and mixtures thereof, most preferred being methylene chloride. Typical total reactant concentrations are in the 5–15% weight range, although complete solvation of 4-(benzyloxy) phenol is not crucial.

Depending on the amount of starting materials, the intermediate forming reaction takes from about 1 to about 16 hours at room temperature and atmospheric pressure. Changing the order of addition of starting materials has no affect on intermediate formation. In general, the reaction can be accelerated and forced to completion via the addition of further quantities of enol ether. After solvent removal a series of washes and triturations with non-polar solvents, typically hexanes, allows purification of the intermediate in high yield, normally greater than about 80%. In the present invention a particular advantage of the use of 4-(benzyloxy)

phenol is that large scale chromatographic purification is not required since any unreacted 4-(benzyloxy)phenol can be conveniently removed with an aqueous sodium hydroxide wash.

B. STEP TWO

Following the formation of said intermediate in step one, step two of the present process involves selective hydrogenolysis of the O-benzyl protecting group. Said hydrogenolysis is accomplished by using any number of hydrogen donors. In the present invention it is preferred that the hydrogen transfer source is non-acidic and is selected from the group consisting of hydrazine, ammonium formate, trialkylammonium formates, and mixtures thereof; all readily available from commercial sources or which can be made prepared prior to reaction. Hydrazine is typically supplied in the hydrate form (55% w/w hydrazine) which can be used without further purification. The molar ratio of hydrogen transfer source to intermediate is from about 6:1 to about 1:1, preferably 4:1 to about 2:1, and most preferably 3:1.

Said hydrogenolysis also requires a supported metal catalyst, preferably a carbon supported metal selected from the group consisting of palladium, platinum, nickel and mixtures thereof Most preferred is palladium on carbon. The weight percentage of metal in the supported catalyst is from about 2–20%, preferably 5–10%.

The reaction is carried out in an organic solvent which fully dissolves the intermediate upon refluxing. The preferred organic solvent is a hydroxy solvent, most preferred are those selected from the group consisting of methanol, ethanol, isopropanol and mixtures thereof, preferably methanol and ethanol. Intermediate concentrations are typically in the 5–15% weight range relative to solvent.

Depending on the amount of starting materials, complete removal of benzyl group generally takes from about 0.5 to about 2.0 hours at reflux under an inert atmosphere. In the present invention a particular advantage of the use of non-acidic hydrogen transfer sources is that large scale chromatographic purification is not required since essentially no hydroquinone or monobenzone byproducts are formed. The product is dried by solvent/water stripping and trituration with non-polar solvents or recrystallization from water/alcohol mixtures.

With regard to this second step involving reaction of the intermediate with said hydrogen donor, it is preferred that said intermediate is substantially free from impurities since they can negatively affect the reaction by, for example, modifying the surface of the preferred metal catalysts used herein.

EXAMPLE I

4-[(Tetrahydrofuran-2-yl)oxy]phenol is prepared as follows:

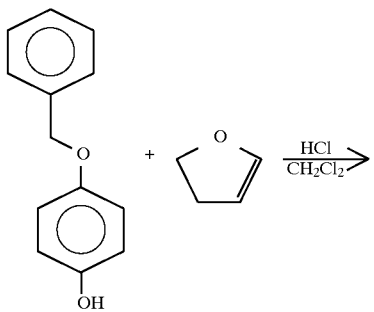

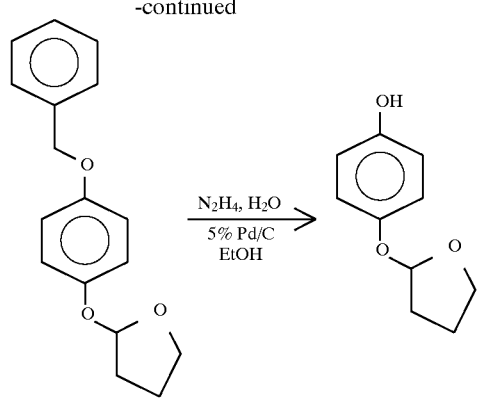

STEP ONE:

Combine 4-(benzyloxy)phenol (34.0 g, 0.17 mol), concentrated hydrochloric acid (0.20 ml, 37%) and 300 ml of methylene chloride. Add to the resulting suspension drop by drop a solution of 2,3-dihydrofuran (22.8 g , 0.33 mol) and 100 ml of methylene chloride. Stir the mixture at room temperature under an inert atmosphere for 16 hours at which time only trace amounts of 4-(benzyloxy)phenol remain by standard thin layer chromatography analysis (Vogel's Textbook of Practical Organic Chemistry, 5th Edition, p.199). Wash the reaction mixture with about three aliquots of 1N sodium hydroxide, each 300 ml, and back extract said aqueous washes with about 200 ml of methylene chloride. Combine the organic layers, dry over sodium sulfate, and concentrate in-vacuo to an oil. Crystallize 2-[(4-benzyloxy) phenoxy]tetrahydrofuran from said oil via careful trituration with a non-polar solvent such as hexanes; melting point 43°–44° C.

STEP TWO:

Add 55% hydrazine hydrate (1.8 g, 30.0 mmol) to a solution comprising 2-[(4-benzyloxy)phenoxy] tetrahydrofuran (2.7 g, 10.0 mmol), 5% Pd/C (0.4 g of 50% wet material) and 50 ml of absolute ethanol. Heat reaction mixture at reflux under an inert atmosphere for about 30 minutes. Cool the reaction mixture and filter off the catalyst. Concentrate the resulting clear pale yellow filtrate to an oil in-vacuo and co-distill in succession with two aliquots of ethanol (50 ml), two aliquots of ethyl acetate (50 ml) and two aliquots of hexanes (50 ml). Triturate the resulting solid with about 25 ml of hexane and dry in-vacuo at 40° C. to constant weight. Composition and purity of the cream colored 4-[tetrahydrofuran-2-yl)oxy]phenol is confirmed by $^1$H and $^{13}$C NMR and elemental analysis; melting point 59°–61° C.

EXAMPLE II

4-[(tetrahydro-2H-pyran-2-yl)oxy]phenol is prepared as follows:

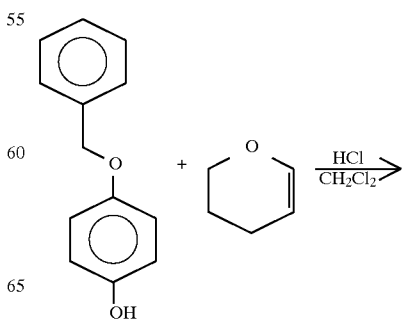

7
-continued

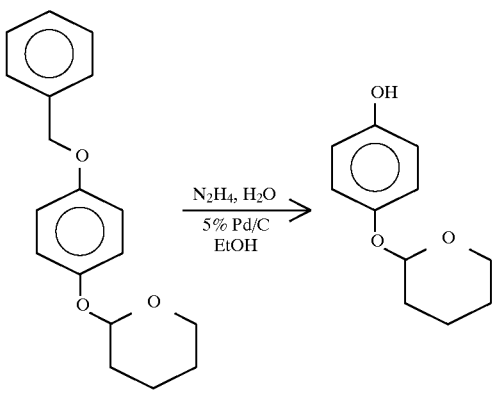

STEP ONE:
Slowly add, under an inert atmosphere, a methylene chloride solution of 3,4-dihydro-2H-pyran (37.3 g, 0.44 mol) to a solution comprising 4-(benzyloxy)phenol (88.8 g, 0.44 mol), concentrated hydrochloric acid (0.25 ml, 37%) and 600 ml of methylene chloride. This reaction mixture is stirred at room temperature for about 15 minutes, at which time a substantial amount of 4-(benzyloxy)phenol is present by thin layer chromatography. Add to the reaction mixture two consecutive portions of a solution comprising 3,4-dihydro-2H-pyran (7.5 g) and 25 ml of methylene chloride. Stir the mixture for about 1 hour wherein only trace amounts of starting phenol remain.

Wash the reaction mixture with about three aliquots of 4% aqueous sodium hydroxide, each 400 ml. Separate the aqueous layer and back extract said layer with about 100 ml of methylene chloride. Combine the organic layers, dry over sodium sulfate, and concentrate in vacuo at about 40° C. to a volume of about 200 ml. Remove excess methylene chloride by co-distilling said concentrate with a sufficient amount of hexane to bring the total volume of the distillate to about 250 ml. Dilute the resulting white suspension with hexane and cool said mixture to about ambient temperature. Collect the precipitated intermediate, 2-[(4-benzyloxy) phenoxy]tetrahydropyran, on a filter and wash in-situ with 100 ml aliquots of hexane. Dry said precipitate in vacuo at about 35° C. until a constant weight is obtained; melting point 70°–71° C.

STEP TWO:
Add 55% hydrazine hydrate (34.85 g, 0.6 mol) to a stirred suspension comprising 2-[(4-benzyloxy)phenoxy] tetrahydropyran (56.4 g, 0.2 mol), 5% Pd/C (4.1 g of 50% wet material) and about 450 ml of absolute ethanol. Slowly heat the reaction mixture and maintain at reflux under an inert atmosphere until thin layer chromatography analysis indicates complete consumption of 2-[(4-benzyloxy) phenoxy]tetrahydropyran. Cool the reaction mixture to about 50° C., clarify said mixture by filtration, and concentrate to a solid in-vacuo at 40° C. Suspend said solid in ethanol and slowly dilute said suspension with de-ionized water. Stir for about 30 minutes and collect the white solid on a filter. Wash said solid in-situ with water, then re-suspend the solid in water. Re-collect the solid, wash in-situ with water and dry in-vacuo at 24° C. to constant weight.

Further purification of 4-[(tetrahydro-2H-pyran-2-yl)oxy] phenol, if necessary, is achieved by a second round of recrystallization from aqueous ethanol. Composition and purity is confirmed by $^1$H and $^{13}$C NMR and elemental analysis; melting point 86°–87° C.

8
EXAMPLE III
4-[(1-butoxyethyl)oxy]phenol is prepared as follows:

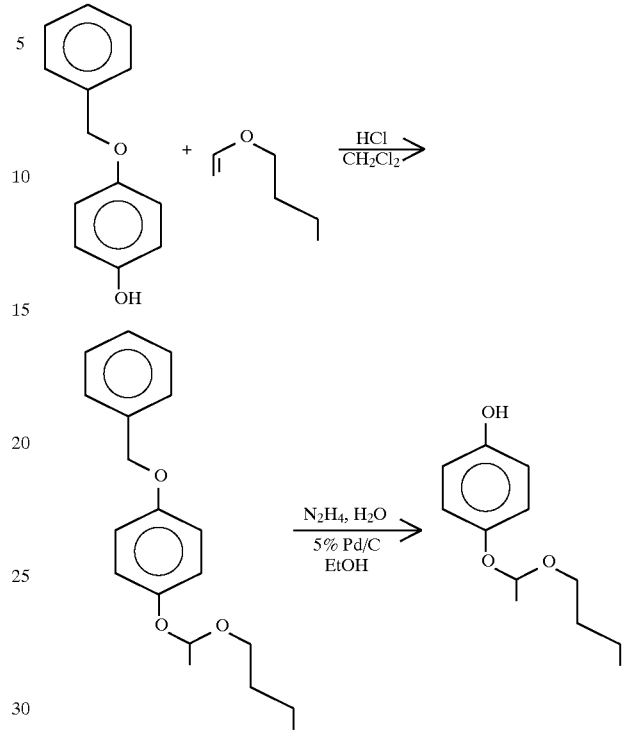

STEP ONE:
In similar fashion to Examples I and II, slowly add a methylene chloride solution of butyl vinyl ether (6.2 g, 0.06 mol) to a solution comprising 4-(benzyloxy)phenol (12.4 g, 0.06 mol), concentrated hydrochloric acid (0.15 ml, 37%) and 100 ml of methylene chloride. Stir under an inert atmosphere for about 2 hours and analyze reaction mixture for 4-(benzyloxy)phenol by thin layer chromatography. If 4-(benzyloxy)phenol is still present, add to said reaction mixture a further portion of butyl vinyl ether (1.8 g, 0.02 mol) in 25 ml of methylene chloride and continue to stir until the phenol is consumed.

Wash the reaction mixture with about three aliquots of 1N sodium hydroxide, each 250 ml, and back extract said aqueous washes with about 100 ml of methylene chloride. Combine the organic layers, dry over sodium sulfate, and concentrate benzyl protected intermediate in-vacuo to a pale yellow oil. Composition and purity of intermediate is confirmed by $^1$H and $^{13}$C NMR.

STEP TWO:
Add 55% hydrazine hydrate (2.5 g, 0.078 mol) to a stirred suspension comprising intermediate from step one (5.0 g, 0.017 mol), 5% Pd/C (3.8 g) and about 100 ml of methanol. Heat the reaction mixture and maintain at reflux under an inert atmosphere for about 2 hours whereupon thin layer chromatography analysis indicates complete consumption of the benzyl protected intermediate. Cool the reaction mixture to room temperature and filter off the catalyst. Concentrate the resulting clear pale yellow filtrate to an oil in-vacuo, wash with hexanes and dry to constant weight in-vacuo at 50° C. Composition and purity of isolated 4-[(1-butoxyethyl)oxy]phenol is confirmed by $^1$H and $^{13}$C NMR.

What is claimed is:
1. The reaction product made by the process comprising the steps of:
   a) reacting monoether of hydroquinone with an enol ether in the presence of an acid catalyst to yield an interme- diate monoacetal of hydroquinone that is protected by an ether protecting group; and b) reacting said intermediate with a hydrogen transfer source in the presence of a metal catalyst such that the ether protecting group is selectively cleaved to thereby provide a reaction mixture rich in hydroquinone monoacetal.

2. The product according to claim 1 wherein the ether protecting group is selected from the group consisting of arylmethyl, diarylmethyl, triarylmethyl, trimethylsilyl ethers and mixtures thereof.

3. The product according to claim 2 wherein the ether protecting group is an arylmethyl ether.

4. The product according to claim 3 wherein the arylmethyl ether is selected from the group consisting of benzyl ethers, aliphatic benzyl ethers and mixtures thereof.

5. The product according to claim 4 wherein the arylmethyl ether is an aliphatic benzyl ether or benzyl ether.

6. The product according to claim 5 wherein the arylmethyl ether is monobenzyl ether.

7. The product according to claim 1 wherein the hydrogen transfer source is non-acidic and selected from the group consisting of hydrazine, ammonium formate, trialkylammonium formates, and mixtures thereof, in a molar ratio of hydrogen transfer source to intermediate from about 6:1 to about 1:1.

8. The product according to claim 7 wherein the hydrogen transfer source is hydrazine in a molar ratio of hydrazine to intermediate product of about 4:1 to about 2:1.

9. The product according to claim 1 wherein the formation of the intermediate is carried out in a polar organic solvent.

10. The product according to claim 9 wherein the polar organic solvent is selected from the group consisting of methylene chloride, diethylether, tetrahydrofuran, dioxane and mixtures thereof.

11. The product according to claim 10 wherein the polar organic solvent is methylene chloride.

12. The product according to claim 1 wherein the metal catalyst is a carbon supported metal selected from the group consisting of palladium, platinum, nickel and mixtures thereof, wherein the weight percentage of metal in the supported catalyst is from about 2–20%.

13. The product according to claim 12 wherein the metal catalyst is palladium on carbon.

14. The product according to claim 1 wherein the reaction of the intermediate and the hydrogen transfer source is carried out in a polar organic solvent.

15. The product according to claim 14 wherein the polar organic solvent is a hydroxy solvent.

16. The product according to claim 15 wherein the hydroxy solvent is selected from the group consisting of methanol, ethanol, isopropanol and mixtures thereof.

17. The product according to claim 16 wherein the hydroxy solvent is methanol or ethanol.

* * * * *